(12) United States Patent
Wada

(10) Patent No.: US 8,467,562 B2
(45) Date of Patent: Jun. 18, 2013

(54) EAR CANAL FITTING UNIT AND BIOLOGICAL SIGNAL MEASURING DEVICE

(75) Inventor: Seiji Wada, Kanagawa (JP)

(73) Assignee: Sony Corporation, Tokyo (JP)

( * ) Notice: Subject to any disclaimer, the term of this patent is extended or adjusted under 35 U.S.C. 154(b) by 617 days.

(21) Appl. No.: 12/719,127

(22) Filed: Mar. 8, 2010

(65) Prior Publication Data

US 2010/0239114 A1 Sep. 23, 2010

(30) Foreign Application Priority Data

Mar. 17, 2009 (JP) ................. P2009-064761

(51) Int. Cl.
*H04R 25/00* (2006.01)
(52) U.S. Cl.
USPC .............. 381/380; 381/322; 381/328
(58) Field of Classification Search
USPC ............ 381/322, 324, 326, 328, 380, 382, 381/60; 181/129, 130, 135; 600/379, 559
See application file for complete search history.

(56) References Cited

U.S. PATENT DOCUMENTS

| 4,029,083 A | 6/1977 | Baylor |
| 4,601,294 A | 7/1986 | Danby et al. |
| 5,673,692 A | 10/1997 | Schulze et al. |
| 7,778,434 B2 * | 8/2010 | Juneau et al. ............ 381/328 |
| 2002/0035340 A1 | 3/2002 | Fraden |
| 2004/0258263 A1 * | 12/2004 | Saxton et al. ............ 381/328 |
| 2007/0093880 A1 | 4/2007 | Reever |

FOREIGN PATENT DOCUMENTS

JP 2008-67911 3/2008

OTHER PUBLICATIONS

European Search Report for corresponding EP 10 00 2307 issued on Jul. 26, 2010.

* cited by examiner

*Primary Examiner* — Huyen D Le
(74) *Attorney, Agent, or Firm* — K&L Gates LLP

(57) ABSTRACT

Disclosed herein is an ear canal fitting unit including: a tube configured to be capable of being inserted into an ear canal; an electrode configured to have flexibility and be so disposed along an outer circumferential surface of the tube that a predetermined gap is formed between the electrode and an inner surface of the ear canal; pressing means for deforming the electrode in such a direction as to get away from the outer circumferential surface of the tube and pressing the electrode against the inner surface of the ear canal; and suppressing means for suppressing push-back of the electrode pressed against the inner surface of the ear canal.

8 Claims, 10 Drawing Sheets

F I G . 1 3
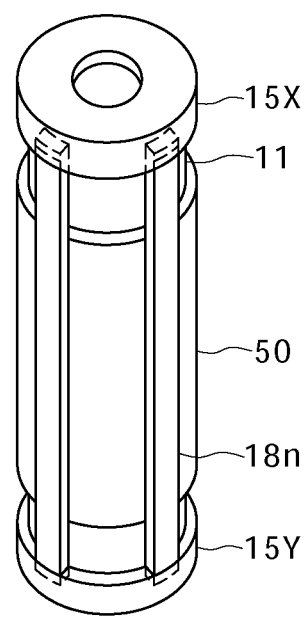

EAR CANAL FITTING UNIT AND BIOLOGICAL SIGNAL MEASURING DEVICE

CROSS REFERENCES TO RELATED APPLICATIONS

The present application claims priority to Japanese Priority Patent Application JP 2009-064761 filed in the Japan Patent Office on Mar. 17, 2009, the entire content of which is hereby incorporated by reference.

BACKGROUND

The present application relates to an ear canal fitting unit and a biological signal measuring device and is suitable for e.g. a technical field of acquiring waves generated and transmitted in a biological body as an electrical signal.

As a related art, there has been proposed an ear canal electrode unit that extracts brain waves or the like by using a spring-shape electrode inserted into an ear canal (refer to e.g. Japanese Patent Laid-open No. 2008-67911).

SUMMARY

Because this spring-shape electrode is inserted into an ear canal, it is so designed as to be located within a range smaller than the inner diameter of the ear canal. Therefore, if the spring-shape electrode is inserted into the ear canal, a gap is formed between the spring-shape electrode and the inner surface of the ear canal, and this gap will cause the extreme lowering of the sensitivity in the extraction of waves transmitted in the biological body as an electrical signal.

On the other hand, when the outer diameter of the spring-shape electrode is closer to the inner diameter of the ear canal, the electrode is inserted into the ear canal in such a state as to be in contact with the inner surface of the ear canal to a higher degree, and the probability of the occurrence of an injury and a pain of the ear canal is higher. Furthermore, the ear canal involves the individual difference and therefore the wearer needs to select the ear canal electrode unit having the spring-shape electrode that fits the wearer. These points will cause low usability.

There is a need for the present application to propose an ear canal fitting unit and a biological signal measuring device that are capable of enhancing the measurement accuracy and have high usability.

According to an embodiment of the present application, there is provided an ear canal fitting unit including a tube configured to be capable of being inserted into an ear canal, and an electrode configured to have flexibility and be so disposed along the outer circumferential surface of the tube that a predetermined gap is formed between the electrode and the inner surface of the ear canal. The ear canal fitting unit further includes a presser configured to deform the electrode in such a direction as to get away from the outer circumferential surface of the tube and press the electrode against the inner surface of the ear canal, and a suppresser configured to suppress push-back of the electrode pressed against the inner surface of the ear canal.

According to another embodiment of the present application, there is provided a biological signal measuring device including an ear hook component configured to have a flexible hook-shape part capable of being hooked on a root of an auricle, an ear canal fitting unit configured to be provided at a leading end part of the hook-shape part and be fitted in an ear canal, and an earlobe attachment configured to be provided at a tail end part of the hook-shape part and be mounted on an earlobe. In the biological signal measuring device, the ear canal fitting unit has a tube capable of being inserted into the ear canal, an electrode that has flexibility and is so disposed along the outer circumferential surface of the tube that a gap is formed between the electrode and the inner surface of the ear canal. The ear canal fitting unit further has a presser that deforms the electrode in such a direction as to get away from the outer circumferential surface of the tube and presses the electrode against the inner surface of the ear canal, and a suppresser that suppresses push-back of the electrode pressed against the inner surface of the ear canal. The earlobe attachment has a reference electrode capable of being attached to the earlobe. The ear hook component has an amplifier that amplifies the potential difference between the electrode and the reference electrode as a biological signal.

In the ear canal fitting unit according to the embodiment of the present application, the electrode is made to abut against the inner surface of the ear canal in such a state that predetermined force is applied to the electrode. Thus, the electrode can be brought into tight contact with the inner surface even when a hair exists on the inner surface and even when the wearer is active, and irrespective of the individual difference. Therefore, this ear canal fitting unit can directly acquire waves transmitted in the wearer as a biological signal without the intermediary of an air layer. As a result, the sensitivity can be dramatically enhanced compared with the case of merely inserting the electrode into the ear canal. Furthermore, the electrode is so inserted that a certain gap exists between the electrode and the inner surface of the ear canal, and thus the contact thereof with the inner surface of the ear canal at the time of the insertion can be reduced. When the electrode is made to abut against the inner surface in such a state that predetermined force is applied to the electrode after the insertion, the electrode can be prevented from rotating and moving toward the deeper side in the ear canal. Consequently, this ear canal fitting unit can provide a comfortable wearing feeling for the wearer and enhance the usability.

Additional features and advantages are described herein, and will be apparent from the following Detailed Description and the figures.

BRIEF DESCRIPTION OF THE FIGURES

FIG. 13 is a diagram schematically showing the configuration of an ear canal fitting unit according to still another embodiment of the present application.

DETAILED DESCRIPTION

The present application will be described below with reference to the drawings according to an embodiment. The description will be made in the following order.
<1. Embodiment>
[1-1. Configuration of Biological Signal Measuring Device]
[1-2. Configuration of Ear Canal Fitting Unit]
[1-3. Configuration of Earlobe Attachment]
[1-4. Wearing Procedure of Biological Signal Measuring Device]
[1-5. Configuration of Signal Processor in Ear Hook Main Body]
[1-6. Advantageous Effects and so on]
<2. Other Embodiments>

1. Embodiment

[1-1. Configuration of Biological Signal Measuring Device]

Figure 1:
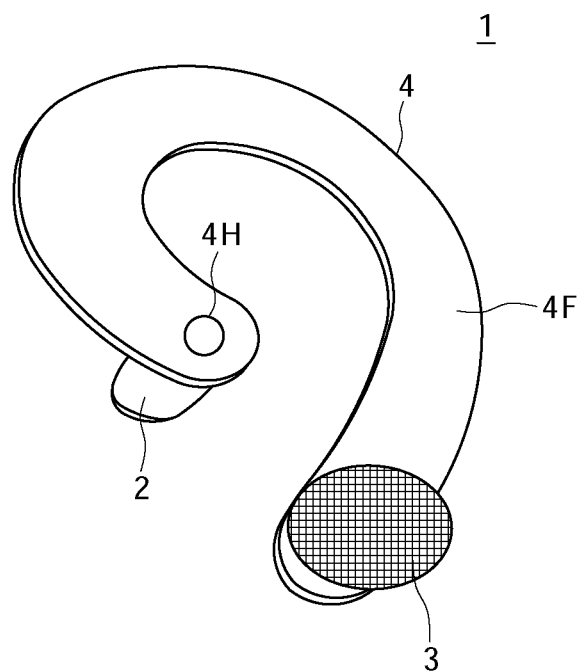
FIG. 1 is a diagram schematically showing the configuration of a biological signal measuring device according to an embodiment of the present application.
Figure 2:
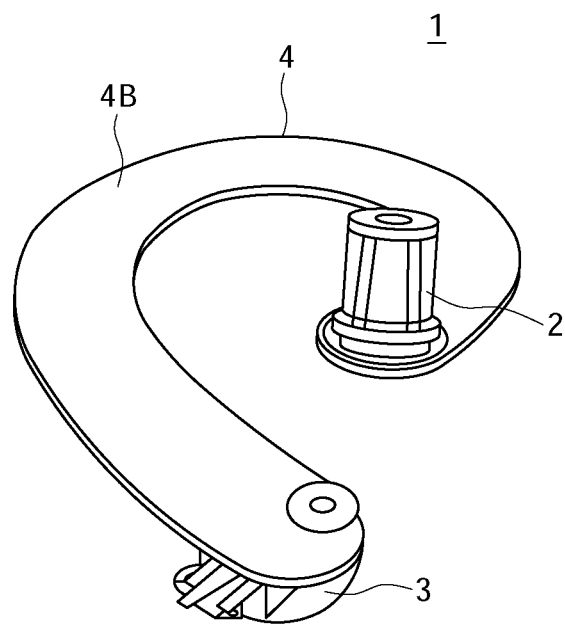
FIG. 2 is a diagram schematically showing the configuration of the biological signal measuring device.

In FIGS. 1 and 2, the configuration of a biological signal measuring device 1 is shown. This biological signal measuring device 1 includes a unit 2 fitted in an ear canal (hereinafter, referred to also as the ear canal fitting unit 2), a unit 3 attached to an earlobe (hereinafter, referred to also as the earlobe attachment 3), and a main body 4 that can be hooked on the root of an ear (auricle) (hereinafter, referred to also as the ear hook main body 4).

The ear hook main body 4 is formed into a hook shape as a whole by using a flexible member composed of e.g. a polyurethane resin. This ear hook main body 4 is so designed that the leading end part thereof is located near the opening of the ear canal and the tail end part thereof is located near the earlobe when the ear hook main body 4 is hooked on the root of the ear (auricle).

A through-hole 4H is provided at the leading end part of the ear hook main body 4, and the ear canal fitting unit 2 is attached to a back surface 4B of the part at which the through-hole 4H is provided (see FIG. 2). On the other hand, the earlobe attachment 3 is attached to a front surface 4F of the tail end part of the ear hook main body 4 (see FIG. 1).

A substrate on which a signal processor is mounted is provided inside the ear hook main body 4, and the ear canal fitting unit 2 and the earlobe attachment 3 are connected to this signal processor.

[1-2. Configuration of Ear Canal Fitting Unit]

Figure 3A:
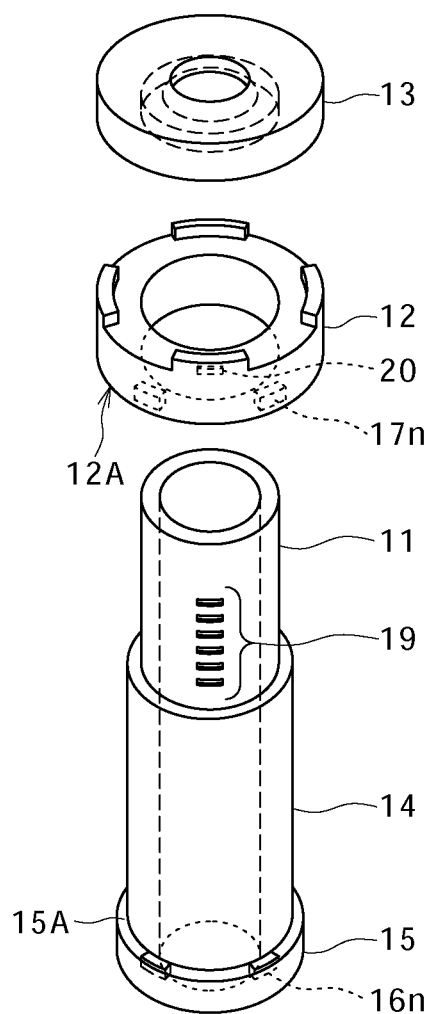
FIGS. 3A and 3B are diagrams schematically showing the configuration of an ear canal fitting unit.
Figure 3B:
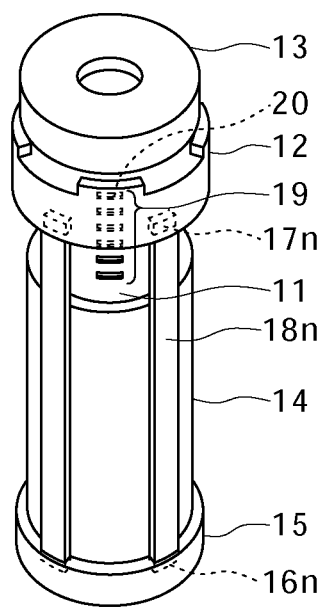

In FIGS. 3A and 3B, the configuration of the ear canal fitting unit 2 is shown. This ear canal fitting unit 2 has a tube-shape base member (hereinafter, referred to also as the base tube) 11. The length of this base tube 11 is set equal to or shorter than the distance from the opening of the ear canal to a position immediately before the position at which the density of nerves starts to greatly increase (the position distant from the eardrum toward the opening side by about two centimeters).

The base tube 11 is inserted in a tube-shape member 12 capable of sliding in the longitudinal direction of the base tube 11 (hereinafter, referred to also as the sliding tube 12). The outer diameter of this sliding tube 12 is set larger than the opening of the ear canal in this embodiment. However, the outer diameter larger than the opening of the ear canal is not an essential requirement.

At one end part of the base tube 11, a tube-shape member 13 for preventing the removal of the sliding tube 12 (hereinafter, referred to also as the tube lid 13) is fitted. This tube lid 13 is fixed to the back surface 4B of the ear hook main body 4 by a fixing component such as an adhesive in such a way that the tube lid 13 is concentric with the through-hole 4H of the ear hook main body 4. The tube lid 13 (i.e. the base tube 11) and the through-hole 4H may have different sectional size and shape. However, it is more preferable that they have the same size and shape.

On the outer circumferential surface of the base tube 11, a tube-shape member 14 for restricting the range of the movement of the sliding tube 12 relative to the base tube 11 (hereinafter, referred to also as the movement range restrictor 14) is provided. A flange 15 is provided at the other end part of the base tube 11. The outer diameter of this flange 15 is set larger than the outer diameter of the movement range restrictor 14 and smaller than the inner diameter of the ear canal.

On a surface 15A opposed to the sliding tube 12, of this flange 15, trenches $16n$ (n is an integer equal to or larger than two) are formed outside the position corresponding to the outer diameter of the movement range restrictor 14 and at predetermined intervals along the outer circumference of the surface 15A. On the other hand, on a surface 12A opposed to the flange 15, of the sliding tube 12, trenches $17n$ are formed at the positions associated with the trenches $16n$ formed in the flange 15.

In these trenches $16n$ and $17n$, the ends of plate-shape electrodes $18n$ having flexibility (hereinafter, referred to also as the flexible electrodes $18n$) are fitted. The length of the flexible electrodes $18n$ is set substantially equal to the distance between the surface 12A of the sliding tube 12 made to abut against the tube lid 13 and the surface 15A of the flange 15.

Therefore, in the state in which the sliding tube 12 abuts against the tube lid 13, the flexible electrodes $18n$ are disposed inside the flange 15, whose outer diameter is smaller than the inner diameter of the ear canal, in such a state as to be parallel and straight to the base tube 11.

Figure 4A:
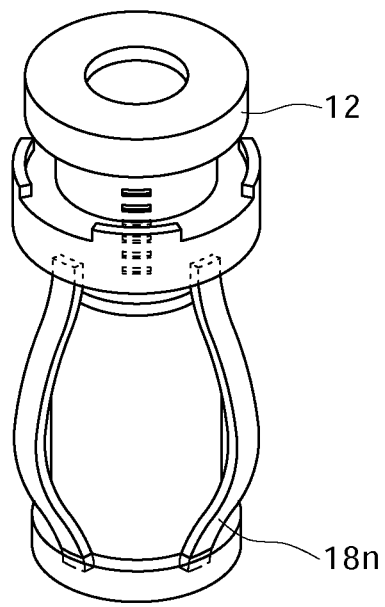
FIGS. 4A and 4B are diagrams schematically showing the deformation of flexible electrodes in linkage with the movement of a sliding tube.
Figure 4B:
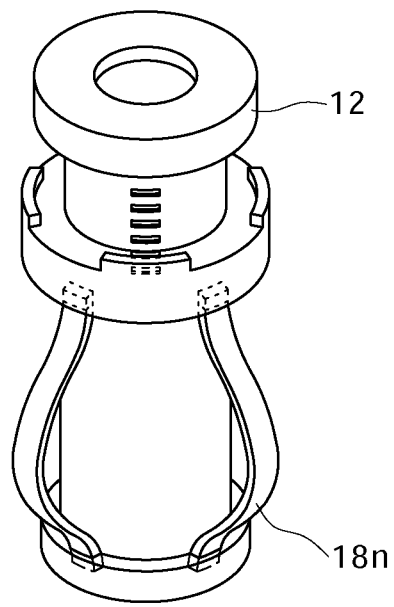

On the other hand, when the sliding tube 12 is moved toward the flange 15 and gets away from the tube lid 13, as shown in FIGS. 4A and 4B, the flexible electrodes $18n$ bend in such a direction as to get away from the outer circumferential surface of the base tube 11 (or the movement range restrictor 14) to a higher degree when the distance between the sliding tube 12 and the tube lid 13 becomes longer. Consequently, the flexible electrodes $18n$ are so disposed as to protrude to the outside of the flange 15, whose outer diameter is smaller than the inner diameter of the ear canal.

In this embodiment, on the outer circumferential surface of the base tube 11, concave trenches 19 for restricting the movement of the sliding tube 12 (hereinafter, referred to also as the movement restriction trenches 19) are formed at predetermined intervals along the longitudinal direction of the base tube 11. Furthermore, on the inner circumferential surface of the sliding tube 12, a protruding claw 20 engaged to the movement restriction trench 19 (hereinafter, referred to also as the engagement claw 20) is formed.

This feature allows the ear canal fitting unit 2 to keep the degree of the bending of the flexible electrodes 18n in a stepwise manner by the movement restriction trenches 19 and the engagement claw 20.

The base tube 11, the movement range restrictor 14, and the flange 15 of the ear canal fitting unit 2 are formed by processing one tube member in such a way that the wall thickness of the tube member is sequentially varied along the direction from one end to the other end of the tube member. Therefore, the number of parts can be reduced and the robustness can be enhanced compared with the case of assembling separate members.

[1-3. Configuration of Earlobe Attachment]

Figure 5:
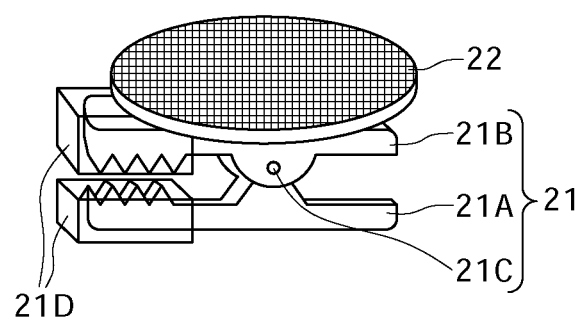
FIG. 5 is a diagram schematically showing the configuration of an earlobe attachment.

In FIG. 5, the schematic configuration of the earlobe attachment 3 is shown. This earlobe attachment 3 has a clip 21 that sandwiches an earlobe for holding the earlobe attachment 3 on the earlobe. In this clip 21, one arm 21A is connected to the other arm 21B via a clip axis 21C.

A buffer member 21D such as sponge or rubber is attached to each of the part made to abut against an earlobe (hereinafter, referred to also as the earlobe abutting part), of one arm 21A, and the earlobe abutting part of the other arm 21B.

The part of one arm 21A on the opposite side to the earlobe abutting part thereof is fixed to the front surface 4F of the tail end part of the ear hook main body 4. The part of the other arm 21B on the opposite side to the earlobe abutting part thereof is connected to an electrode 22 serving as the basis (hereinafter, referred to also as the earth electrode 22). This earth electrode 22 has a coin shape comparable in surface area to the earlobe and is used also as the part directly held by fingers or the like.

[1-4. Wearing Procedure of Biological Signal Measuring Device]

Figure 6:
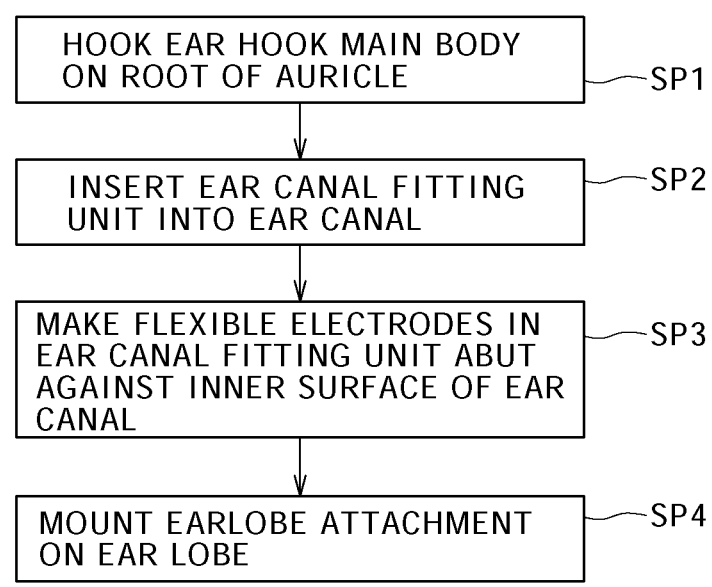
FIG. 6 is a flowchart showing the wearing procedure of the biological signal measuring device.

In FIG. 6, one example of the wearing procedure of the biological signal measuring device 1 is shown. Initially, in a first step SP1, the ear hook main body 4 is hooked on the root of an ear (auricle).

This ear hook main body 4 is formed by using a flexible member composed of a polyurethane resin or the like and thus can be easily hooked without giving the wearer a feeling of uncomfortable.

Figure 7:
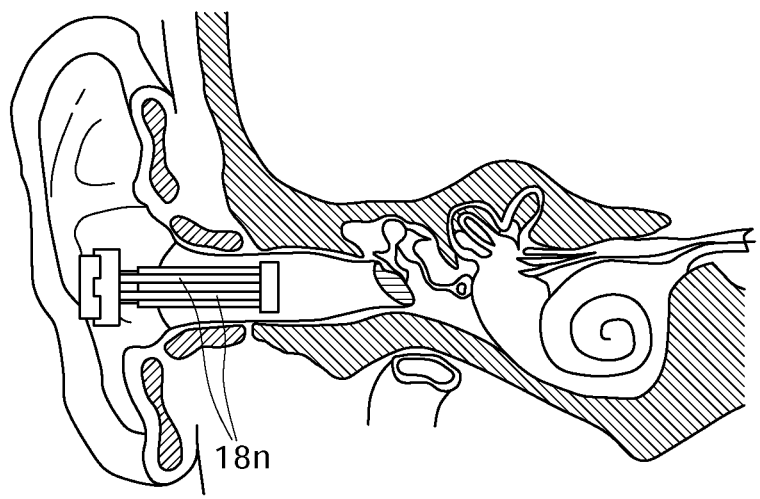
FIG. 7 is a schematic diagram for explaining insertion of the ear canal fitting unit.

In a second step SP2, as shown in FIG. 7, the ear canal fitting unit 2 is inserted into the ear canal in such a state that the sliding tube 12 abuts against the tube lid 13.

In the state in which the sliding tube 12 abuts against the tube lid 13, the flexible electrodes 18n are located inside the flange 15 having an outer diameter smaller than the inner diameter of the ear canal, and the leading end part of the ear hook main body 4 hooked on the root of the auricle is located near the opening of the ear canal. Thus, this biological signal measuring device 1 allows the ear canal fitting unit 2 to be inserted into the ear canal intuitively and rapidly in such a way that the tip side on which the flange 15 is formed is set on the front side in the insertion direction.

Furthermore, the outer diameter of the sliding tube 12 is set larger than the opening of the ear canal. Thus, this biological signal measuring device 1 can prevent the tip of the ear canal fitting unit 2 from reaching the position at which the density of nerves is high in the ear canal.

Figure 8:
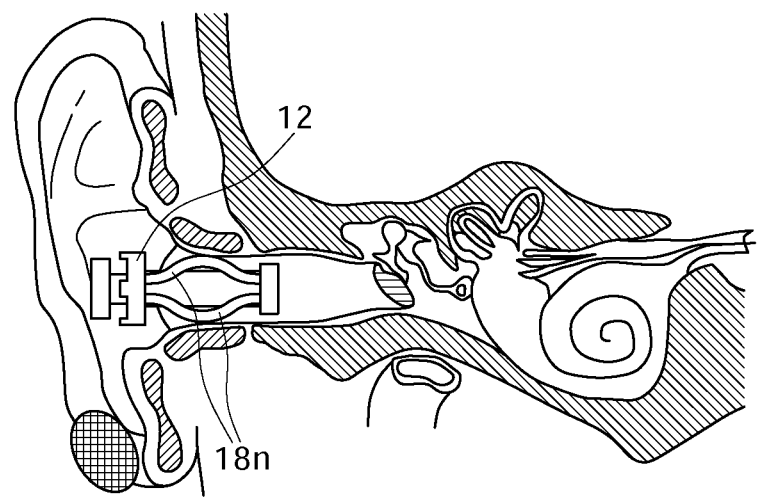
FIG. 8 is a schematic diagram for explaining the abutting of the flexible electrodes against the inner surface of an ear canal.

In a third step SP3, the sliding tube 12 is moved toward the flange 15. Consequently, as shown in FIG. 8, the engagement claw 20 is engaged to the movement restriction trench 19 at such a position that the flexible electrodes 18n are pressed against the inner surface of the ear canal.

The flexible electrodes 18n have such a structure as to bend to the outside of the flange 15 to a higher degree when the distance between the sliding tube 12 and the tube lid 13 becomes longer (see FIGS. 4A and 4B). Thus, this ear canal fitting unit 2 allows the flexible electrodes 18n to abut against the inner surface of the ear canal irrespective of the individual difference of the ear canal shape.

Furthermore, the degree of the bending of the flexible electrodes 18n is kept in a stepwise manner by the movement restriction trenches 19 and the engagement claw 20 (see FIGS. 4A and 4B). Thus, this ear canal fitting unit 2 can adjust the pressure of the contact of the flexible electrodes 18n with the inner surface of the ear canal. As a result, the contact pressure can be set to a value that offers such a feeling of wearing that the wearer feels no pain.

In a fourth step SP4, the clip 21 in the earlobe attachment 3 sandwiches the earlobe for holding the earlobe attachment 3 on the earlobe. The tail end part of the ear hook main body 4 hooked on the root of the auricle is located near the earlobe. Therefore, this biological signal measuring device 1 allows the earlobe attachment 3 to be held on the earlobe intuitively and rapidly through the sandwiching of the earlobe by the clip 21. The earth electrode 22 has a coin shape comparable in size to the earlobe, which allows the wearer to easily hold the earth electrode 22 when sandwiching the earlobe by the clip 21.

In addition, the buffer member 21D is attached to the earlobe abutting parts of the arms 21A and 21B in the clip 21. Therefore, the earlobe attachment 3 can offer such a feeling of wearing that the wearer feels no pain.

Figure 9:
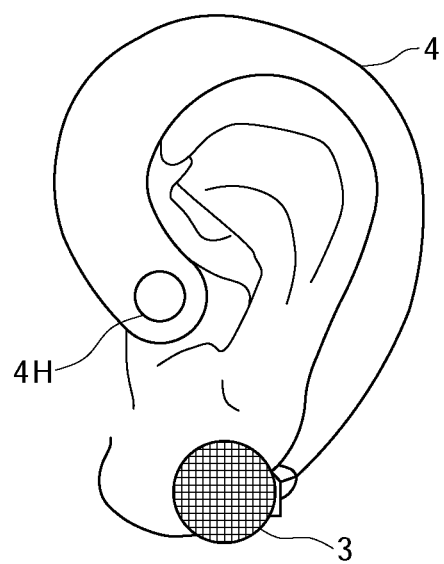
FIG. 9 is a diagram schematically showing the wearing state of the biological signal measuring device.

Through the above-described wearing procedure, the biological signal measuring device 1 is mounted on the ear as shown in FIG. 9. However, the above described wearing order is merely an example, and the wearing order is not limited thereto.

A hollow state is made inside the ear canal fitting unit 2 (see FIG. 3A and so on), and this hollow is made to communicate with the through-hole 4H of the ear hook main body 4. Thus, even when being mounted on an ear of the wearer, the biological signal measuring device 1 avoids the complete covering of the ear and prevents loss of hearing. Therefore, this biological signal measuring device 1 can measure biological information without impairing a feeling of comfort.

[1-5. Configuration of Signal Processor in Ear Hook Main Body]

Figure 10:
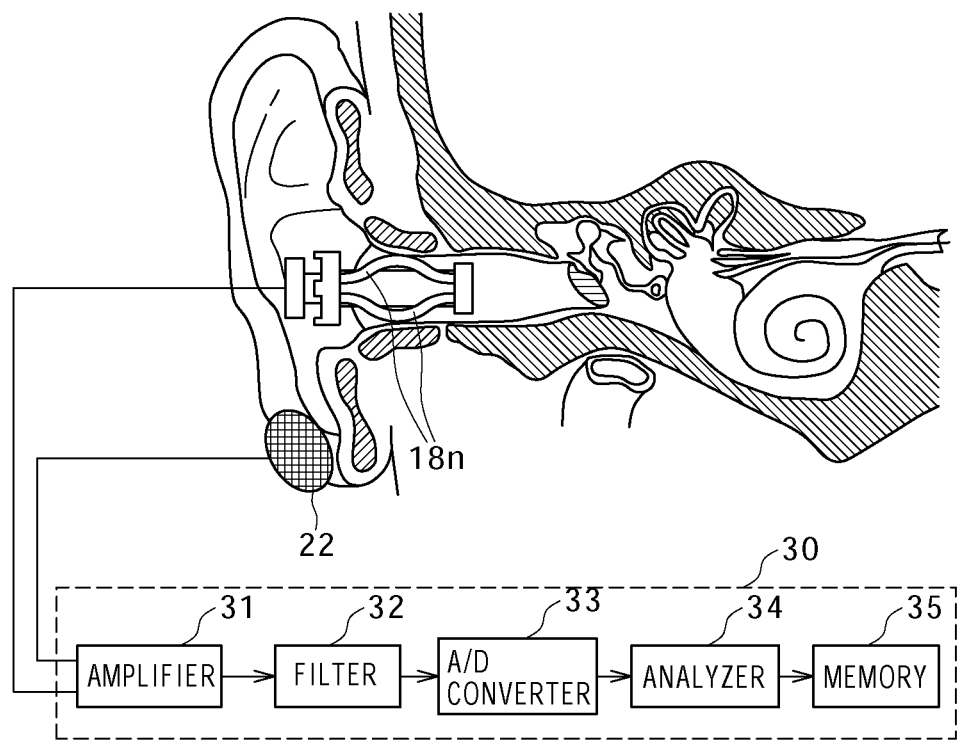
FIG. 10 is a block diagram showing the configuration of a signal processor.

In FIG. 10, the configuration of a signal processor 30 in the ear hook main body 4 is shown. This signal processor 30 includes an amplifier 31, a filter 32, an A/D (analog/digital) converter 33, an analyzer 34, and a memory 35. As the memory 35, not only one included in the ear hook main body 4 but also a removable memory such as a USB (Universal Serial Bus) memory, an SD card memory, or a CF (Compact-Flash) card memory can be employed.

For example, when the signal processor 30 receives a measurement start command from an operating unit provided on the surface of the ear hook main body 4, it provides the supply voltage from a battery or the like to the respective units 31 to 35. When the signal processor 30 receives a measurement stop command from the operating unit, it cuts off the provision of the supply voltage.

The amplifier 31 amplifies the potential difference between the flexible electrodes 18n of the ear canal fitting unit 2 and the earth electrode 22 of the earlobe attachment 3 as a biological signal, and gives the amplified biological signal to the filter 32.

The flexible electrodes 18n are made to abut against the inner surface of the ear canal in such a state that predetermined force is applied to the flexible electrodes 18n (see FIG. 8). Thus, the amplifier 31 can directly sense waves transmitted in the wearer as the potential difference. As a result, the sensitivity can be dramatically enhanced compared with the case of merely inserting the flexible electrodes 18n into the ear canal.

Furthermore, in contrast to the flexible electrodes 18n, which are located on the inner surface of the ear canal, the earth electrode 22 is located on the earlobe, which is outside the ear canal. Therefore, long distance is ensured as the distance between the electrodes compared with e.g. the case in which both the electrodes are located in the ear canal. This allows the amplifier 31 to sense waves in the head of the wearer as the potential difference extensively. As a result, the target biological signal can be accurately acquired.

For the filter 32, the frequency bands that should be covered as the measurement subject are set. The filter 32 removes signal components other than those in the set frequency bands and gives the biological signal resulting from this removal to the A/D converter 33.

In this embodiment, the frequency bands that should be covered as the measurement subject are those corresponding to brain waves. Therefore, the biological signal from which signal components other than those in the frequency bands corresponding to brain waves are removed (hereinafter, referred to also as the brain wave signal) is given to the A/D converter 33.

The brain waves and the corresponding frequency bands are as follows: delta wave (1 to 3 Hz), theta wave (4 to 7 Hz), alpha wave (8 to 13 Hz), beta wave (14 to 30 Hz), gamma wave (31 to 64 Hz), omega wave (65 to 128 Hz), rho wave (129 to 512 Hz), and sigma wave (513 to 1024 Hz). Part or all of them are variably set as the frequency bands that should be covered as the measurement subject by the predetermined operating unit.

The A/D converter 33 converts the brain wave signal to digital data (hereinafter, referred to also as the brain wave data) and gives the brain wave data to the analyzer 34.

The analyzer 34 includes a CPU, a ROM, and a RAM serving as the work memory for the CPU. In this ROM, a program for execution of analysis processing and data indicating the level under which the flexible electrodes 18n should be regarded as being not in contact with the inner surface of the ear canal (hereinafter, this level will be referred to also as the non-contact level threshold) are stored.

When receiving a measurement start command, the analyzer 34 expands the program stored in the ROM in the RAM and executes various kinds of processing in accordance with the program. Specifically, the analyzer 34 compares the non-contact level threshold with the average of the level of the brain wave data given from the A/D converter 33 in a predetermined period from the measurement start timing (hereinafter, referred to also as the calibration period).

If this level average is lower than the non-contact level threshold, the analyzer 34 regards the flexible electrodes 18n as being not in contact with the inner surface of the ear canal, and notifies the wearer of that the ear canal fitting unit 2 should be set again through a speaker (not shown) attached to the ear canal fitting unit 2.

On the other hand, if the level average is equal to or higher than the non-contact level threshold, the analyzer 34 regards the flexible electrodes 18n as being in contact with the inner surface of the ear canal, and stores the brain wave data given from the A/D converter 33 in the memory 35.

Furthermore, if the level average is equal to or higher than the non-contact level threshold, the analyzer 34 determines whether the present sleep stage is a non-REM sleep stage or a REM sleep stage based on the brain wave data given from the A/D converter 33, and associates the determination result with the brain wave data.

The stage determination is so made that e.g. the appearance ratio of the delta wave, theta wave, alpha wave, or the like per unit time and the duration of the predetermined appearance ratio are employed as the determination factors.

[1-6. Advantageous Effects and so on]

In the above-described configuration, by the sliding tube 12, which slides on the outer circumferential surface of the base tube 11 parallel to the longitudinal direction of the base tube 11, the ear canal fitting unit 2 outwardly bends the flexible electrodes 18n disposed between the sliding tube 12 and one end of the base tube 11 and presses them against the inner surface of an ear canal.

This ear canal fitting unit 2 makes the flexible electrodes 18n abut against the inner surface of the ear canal in such a state that predetermined force is applied to the flexible electrodes 18n (see FIG. 8), and thus can bring the flexible electrodes 18n into tight contact with the inner surface even when a hair exists on the inner surface and even when the wearer is active.

Consequently, this ear canal fitting unit 2 can directly acquire waves transmitted in the wearer as a biological signal without the intermediary of an air layer. As a result, the sensitivity can be dramatically enhanced compared with the case of merely inserting the flexible electrodes 18n into the ear canal. In addition, the ear canal fitting unit 2 can prevent the flexible electrodes 18n from rotating and moving toward the deeper side in the ear canal. As a result, a good wearing feeling for the wearer can be provided.

The flexible electrodes 18n are so inserted that a certain gap exists between the flexible electrodes 18n and the inner surface of the ear canal. Thus, the contact thereof with the inner surface of the ear canal at the time of the insertion can be reduced. On the other hand, when the flexible electrodes 18n are made to abut against the inner surface in such a state that predetermined force is applied to the flexible electrodes 18n after the insertion, the electrodes can be prevented from rotating and moving toward the deeper side in the ear canal.

Furthermore, this ear canal fitting unit 2 can adjust the degree of pressing of the flexible electrodes 18n against the inner surface of the ear canal based on the amount of slide of the sliding tube 12 (see FIGS. 4A and 4B), and thus can press the flexible electrodes 18n irrespective of the individual difference of the wearer. In addition, the ear canal fitting unit 2 can press the flexible electrodes 18n without pain and so on, which can provide a good wearing feeling for the wearer.

Moreover, this ear canal fitting unit 2 has a speaker and a message is notified from this speaker if the electrodes are not in contact with the inner surface of the ear canal or that is possible. Therefore, this ear canal fitting unit 2 can prevent measurement in the state in which the sensitivity to a biological signal is lowered. As a result, the measurement accuracy can be enhanced.

Because this ear canal fitting unit 2 is provided on the ear hook main body 4 (see FIG. 1 or FIG. 2), e.g. dropping thereof at the time of insertion or removal thereof into/from an ear canal can be prevented. Furthermore, interconnection connected to the flexible electrodes 18n can be housed inside the ear hook main body 4. Therefore, the ear canal fitting unit 2 can avoid the following troubles: the ear canal fitting unit 2 itself is lost e.g. at the time of insertion or removal thereof into/from an ear canal; and the ear canal fitting unit 2 gets entangled in a cord. This allows enhancement in the usability.

2. Other Embodiments

In the above-described embodiment, the sliding tube 12, which slides on the outer circumferential surface of the base tube 11 parallel to the longitudinal direction of the base tube 11, deforms the flexible electrodes 18n in such a direction as to get away from the outer circumferential surface of the base tube 11 and presses them against the inner surface of an ear canal.

However, the means for deforming the electrode in such a direction as to get away from the outer circumferential surface of the tube and pressing it against the inner surface of an ear canal is not limited to this embodiment, but other embodiments of the present application can be employed.

Figure 11A:
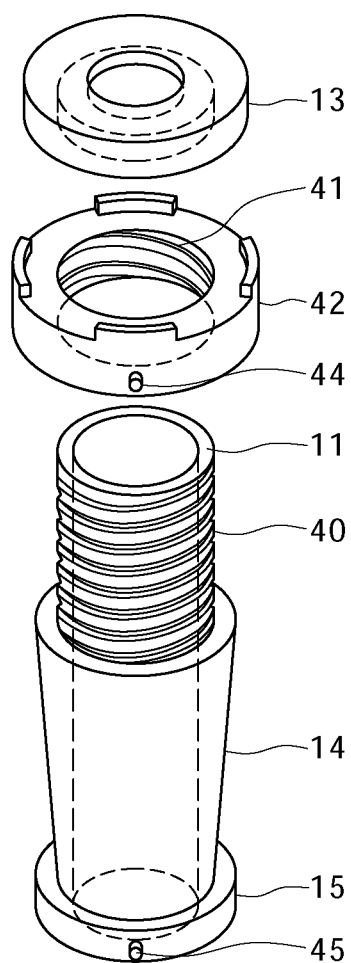
FIGS. 11A and 11B are diagrams schematically showing the configuration of an ear canal fitting unit according to another embodiment of the present application.
Figure 11B:
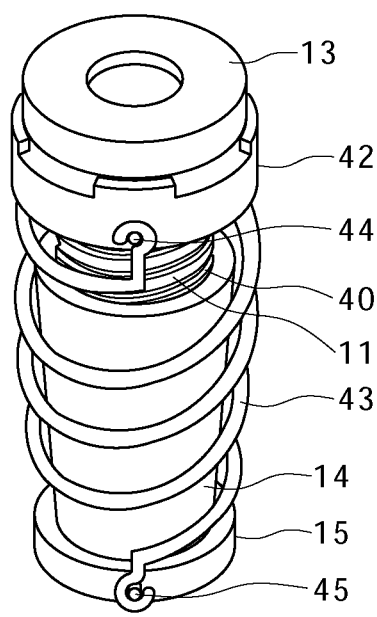

For example, in FIGS. 11A and 11B, in which the part corresponding to that in FIGS. 3A and 3B is given the same numeral, the configuration of an ear canal fitting unit according to another embodiment of the present application is shown. In this ear canal fitting unit, a screw groove 40 is formed on the outer circumferential surface of a base tube 11. A sliding tube 42 having a screw groove 41 that fits the screw groove 40 on its inner circumferential surface slides on the outer circumferential surface of the base tube 11 along the screw groove 40 in a screw manner. The outer diameter of this sliding tube 42 is set substantially equal to that of a flange 15.

Around the base tube 11, an electrode 43 that has flexibility and is wound in a spiral manner with a predetermined pitch along the outer circumferential surface of a movement range restrictor 14 (hereinafter, referred to also as the spring electrode 43) is disposed. The outer diameter of this spring electrode 43 is set smaller than the inner diameter of the ear canal. One end of the spring electrode 43 is hooked on a projection 44 formed on the outer circumferential surface of the sliding tube 42, and the other end thereof is hooked on a projection 45 formed on the outer circumferential surface of the flange 15.

Figure 12:
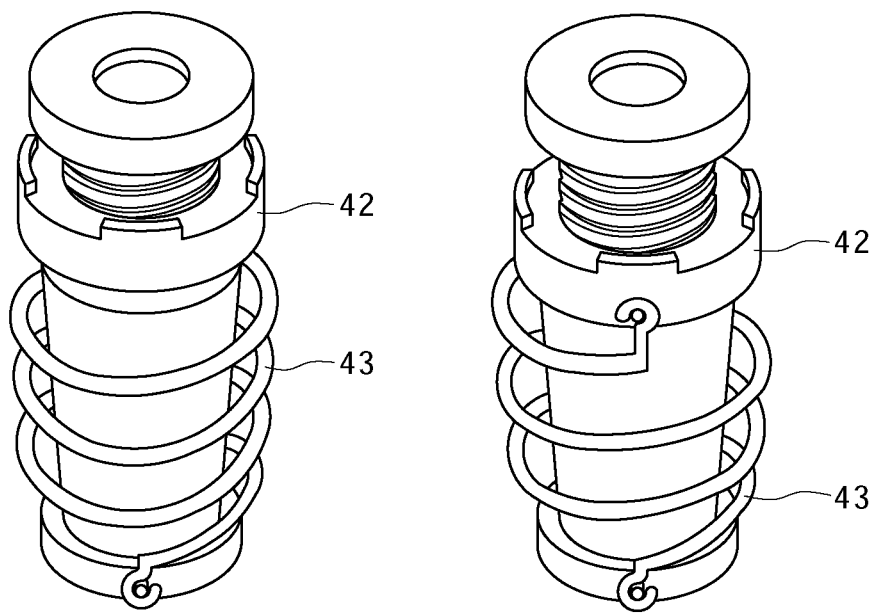
FIG. 12 is a diagram schematically showing the deformation of a spring electrode in linkage with the movement of a sliding tube.

The winding direction of this spring electrode 43 is set opposite to the sliding direction of the sliding tube 42, which slides in a screw manner, (the winding direction of the screw groove 40). Therefore, if the sliding tube 42 is moved toward the flange 15 and gets away from a tube lid 13, as shown in FIG. 12, the spring electrode 43 is displaced in such a direction as to get away from the outer circumferential surface of the base tube 11 (or the movement range restrictor 14) to a higher degree when the distance between the sliding tube 42 and the tube lid 13 becomes longer.

As above, this ear canal fitting unit is so configured that the sliding tube 42, which slides on the outer circumferential surface of the base tube 11 in a screw manner, outwardly displaces the spring electrode 43 wound in the opposite direction of the sliding direction of the sliding tube 42 and presses it against the inner surface of an ear canal. Because the contact area of the electrode with respect to the inner surface of the ear canal per unit length is larger compared with the ear canal fitting unit 2, this ear canal fitting unit is more advantageous in view of the sensitivity of sensing of biological information.

As another example, in the ear canal fitting unit 2, the spring electrode 43 and the projections 44 and 45 may be employed instead of the flexible electrodes 18n and the trenches 16n and 17n. Furthermore, in the ear canal fitting unit 2, flexible electrodes having a tube shape may be employed instead of the flexible electrodes 18n.

As another example, the configuration of an ear canal fitting unit according to another embodiment of the present application is shown in FIG. 13, in which the part corresponding to that in FIG. 3 is given the same numeral. In this ear canal fitting unit, flanges 15X and 15Y whose outer diameter is smaller than the inner diameter of the ear canal are provided at both ends of a base tube 11, and flexible electrodes 18n are fixed between the flanges 15X and 15Y.

A tube 50 is provided between the flexible electrodes 18n and the outer circumferential surface of the base tube 11. To the tube 50, a gas injector for injecting a gas is connected. This gas injector is provided on an ear hook main body 4 for example.

Therefore, if a gas is injected from the gas injector to the tube 50, the flexible electrodes 18n bend in such a direction as to get away from the outer circumferential surface of the base tube 11 in linkage with the tube 50 that swells due to the gas injection.

In this manner, in this ear canal fitting unit, the tube 50 provided between the outer circumferential surface of the base tube 11 and the flexible electrodes 18n and the gas injector for injecting a gas into the tube 50 are so configured that the flexible electrodes 18n are bent into a bow shape and pressed against the inner surface of an ear canal.

The flexible electrodes 18n in this ear canal fitting unit may be replaced by flexible electrodes having a tube shape or may be replaced by the spring electrode 43.

Figure 14A:
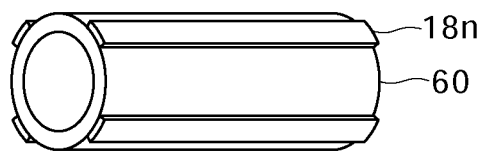
FIGS. 14A to 14D are diagrams schematically showing the configuration of an ear canal fitting unit according to yet another embodiment of the present application.

As another example, an ear canal fitting unit shown in FIG. 14A may be employed. This ear canal fitting unit includes a base tube 60 that is composed of a sponge material and has an inner diameter larger than the inner diameter of the ear canal, and flexible electrodes 18n bonded to the outer circumferential surface of this base tube at predetermined intervals.

Figure 14B:
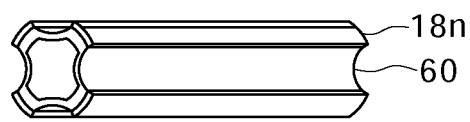
Figure 14C:
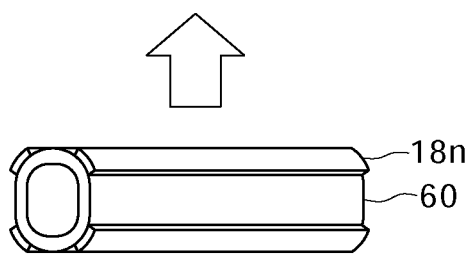
Figure 14D:
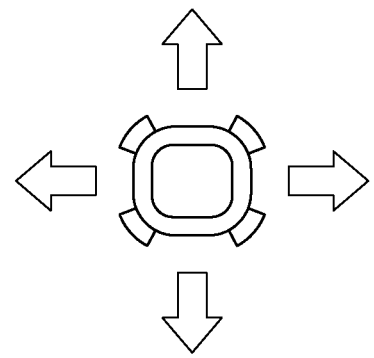

This ear canal fitting unit is inserted into an ear canal in such a state that the base tube 60 is compressed to a size smaller than the inner diameter of the ear canal (see FIG. 14B). The flexible electrodes 18n move in such a manner as to spread toward the inner surface of the ear canal due to force of the reversion of the base tube 60 to its original state (see FIGS. 14C and 14D).

In this manner, in this ear canal fitting unit, the force of the reversion of the base tube 60 itself composed of a sponge material to its original state makes the flexible electrodes 18n be displaced in such a direction as to get away from the outer circumferential surface of the base tube 60 and be pressed against the inner surface of the ear canal. This ear canal fitting unit can be used by only operation of compressing and inserting the base tube 60 and has a smaller number of parts compared with the ear canal fitting unit 2. Therefore, this ear canal fitting unit is advantageous in view of the usability and simplification of the configuration.

As the means for deforming the electrode in such a direction as to get away from the outer circumferential surface of the tube and pressing it against the inner surface of an ear canal, one other than those of these examples can be employed as long as it does not depart from the effect of the means.

In the above-described embodiment, the movement restriction trenches 19 provided on the outer circumferential surface of the base tube 11 at predetermined intervals along the longitudinal direction of the base tube 11 and the engagement claw 20 provided on the inner circumferential surface of the sliding tube 12 suppress push-back of the flexible electrodes 18n pressed against the inner surface of an ear canal.

However, the means for suppressing push-back of the electrode pressed against the inner surface of an ear canal is not limited to this embodiment, but other embodiments of the present application can be employed.

For example, in the ear canal fitting unit shown in FIG. 11, when the spring electrode 43 is pressed against the inner surface of an ear canal, the stress thereof arises in the direction toward the tube lid 13 via the spring electrode 43 and the sliding tube 42. This direction intersects with the direction of the screw groove 40 formed on the outer circumferential surface of the base tube 11 in a spiral manner and the screw groove 41 formed on the inner circumferential surface of the sliding tube 42 in matching with the screw groove 40. Thus, the sliding tube 42 is made still at this position.

In this manner, in this ear canal fitting unit, the screw groove 40 formed on the outer circumferential surface of the base tube 11 in a spiral manner and the screw groove 41 formed on the inner circumferential surface of the sliding tube 42 in matching with the screw groove 40 suppress push-back of the spring electrode 43. However, a mechanism for releasably fixing the position of the sliding tube 42 may be provided in addition to the screw grooves 40 and 41.

As another example, in the ear canal fitting unit shown in FIG. 13, a valve (not shown) is provided at the connecting part between the tube 50 and the air injector for injecting a gas into the tube 50, and the valve shuts the connecting part when the amount of gas in the tube 50 reaches the amount of gas that should be injected. In this manner, in this ear canal fitting unit, the valve suppresses push-back of the flexible electrodes 18n.

As another example, in the ear canal fitting unit shown in FIG. 14, the force of the reversion of the base tube 60 itself composed of a sponge material to its original state suppresses push-back of the flexible electrodes 18n.

As the means for suppressing push-back of the electrode pressed against the inner surface of an ear canal, one other than those of these examples can be employed as long as it does not depart from the effect of the means.

In the above-described embodiment, the earth electrode 22 is attached to the clip 21. However, the clip 21 itself may be used as the reference electrode. In addition, the earth electrode 22 may be configured detachably from the clip 21.

In the above-described embodiment, the shape of the sliding tube 12 or 42 is a tube shape. However, it may have a shape that allows fitting in the cavum conchae part. If this is employed, the sliding tube 12 or 42 fitted in the cavum conchae part can avoid the shift and rotation of the electrode pressed against the inner surface of the ear canal, and thus the electrode can be pressed against the inner surface of the ear canal more stably and tightly.

In the above-described embodiment, the ear hook main body 4 has a hook shape as a whole. However, it may be any as long as it has the hook-shape part.

In the above-described embodiment, the measurement subject is brain waves. However, the measurement subject may be myopotentials, and a configuration that allows switching between brain waves and myopotentials may be employed. If the measurement subject is myopotentials, frequency bands corresponding to myopotentials are set for the filter 32, and the filter 32 removes signal components other than those in the frequency bands. Furthermore, the analyzer 34 compares data indicating the myopotential-data limit level under which the flexible electrodes 18n should be regarded as being not in contact with the inner surface of an ear canal (non-contact level threshold) with the average of the level of myopotential data given from the A/D converter 33 in a calibration period.

If this configuration is employed, myopotentials can be treated as the measurement subject similarly to the above-described embodiment. It is possible to employ a configuration in which frequency bands are set by an operating unit provided on the surface of the ear hook main body 4 for example, and it is also possible to employ a configuration in which the setting of the non-contact level threshold is automatically switched depending on the setting of the frequency bands.

In the above-described embodiment, the mounting subject of the biological signal measuring device 1 is a single ear. However, the mounting subject may be both ears. In this case, the analyzer 34 and the memory 35 are omitted in the signal processor 30 in the biological signal measuring device 1 whose mounting subject is one of ears. The conversion result in the A/D converter 33 in this signal processor 30 is given to the analyzer 34 in the signal processor 30 in the biological signal measuring device 1 whose mounting subject is the other of the ears.

The frequency bands that should be set as the measurement subject may be the same between the filter 32 in the signal processor 30 in the biological signal measuring device 1 whose mounting subject is one of ears and the filter 32 in the signal processor 30 in the biological signal measuring device 1 whose mounting subject is the other of the ears, or alternatively may be different therebetween.

If the frequency bands are set the same therebetween, the analyzer 34 may have such a configuration as to calculate the logical OR of brain wave data (or myopotential data) given from one A/D converter 33 and brain wave data (or myopotential data) given from the other A/D converter 33. In this case, by the addition of the respective brain wave data (or myopotential data), the S/N ratio of the brain wave data (or myopotential data) to be stored in the memory 35 is enhanced.

On the other hand, if the frequency bands are made different, the analyzer 34 stores brain wave data given from one A/D converter 33 in the memory 35, and associates myopotential data given from the other A/D converter 33 with the brain wave data to store the myopotential data in the memory 35. Furthermore, for example, it is also possible to determine the awaking state and the facial expression based on myopotential data and associate the determination result with brain wave data. This association can be used as an index for specifying a sleep disorder and a disease.

It is also possible to add the body temperature or the pulse to brain waves and myopotentials as the measurement subject. In this case, a body temperature sensor or a pulse sensor of e.g. an optical system is provided for the ear canal fitting unit, and a signal given from the sensor is supplied to the analyzer 34 via the A/D converter 33. The analyzer 34 associates body temperature data or pulse data with brain wave data and stores the data in the memory 35. This association can be used as an index for specifying a sleep disorder and a disease.

In the above-described embodiment, the electrode is pressed directly against the inner surface of an ear canal. However, to this electrode, a contact medium for efficiently transmitting waves, such as water, oil, or glycerin, may be applied. A mechanism for providing the contact medium to the electrode may be provided. For example, the following configuration may be employed. A container for storing the contact medium is provided in the ear hook main body 4. A needle-shape tube member for providing the contact medium to the electrode is connected to a valve provided in the container, and the tip of the tube member is disposed at one end part of the electrode.

The embodiments of the present application can be possibly used in the medical industry, the game industry, and so on.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. An ear canal fitting unit comprising:
   a tube configured to be capable of being inserted into an ear canal;
   an electrode configured to have flexibility and be so disposed along an outer circumferential surface of the tube that a predetermined gap is formed between the electrode and an inner surface of the ear canal;

pressing means for deforming the electrode in such a direction as to get away from the outer circumferential surface of the tube and pressing the electrode against the inner surface of the ear canal; and suppressing means for suppressing push-back of the electrode pressed against the inner surface of the ear canal, wherein one end of the electrode is fixed to one end part of the tube, the pressing means is formed of a member that slides on the outer circumferential surface of the tube in a longitudinal direction of the tube, and the other end of the electrode is fixed to the member, the suppressing means switches a degree of suppression of push-back in a stepwise manner and is formed of a mechanism for releasably fixing a position of the member, the member has a tube shape and has such a shape as to be fitted in a cavum conchae, the ear canal fitting unit is provided at a leading end of a hook-shape member capable of being hooked on a root of an auricle, and the hook-shape member is provided with an amplifier that amplifies potential difference between the electrode and a reference electrode provided at a tail end of the hook-shape member attachably to an earlobe.

2. An ear canal fitting unit comprising:

a tube configured to be capable of being inserted into an ear canal;

an electrode configured to have flexibility and be so disposed along an outer circumferential surface of the tube that a predetermined gap is formed between the electrode and an inner surface of the ear canal;

pressing means for deforming the electrode in such a direction as to get away from the outer circumferential surface of the tube and pressing the electrode against the inner surface of the ear canal; and suppressing means for suppressing push-back of the electrode pressed against the inner surface of the ear canal, wherein the suppressing means switches a degree of suppression of push-back in a stepwise manner, the electrode is wound along the outer circumferential surface of the tube in a spiral manner, and one end of the electrode is fixed to one end part of the tube, the pressing means is formed of a tube-shape member that slides in a screw manner on the outer circumferential surface of the tube in an opposite direction of a direction of winding of the electrode, and the other end of the electrode is fixed to the tube-shape member, and the suppressing means is formed of a first groove formed on the outer circumferential surface of the tube in a spiral manner and a second groove formed on an inner circumferential surface of the tube-shape member in matching with the first groove.

3. The ear canal fitting unit according to claim 2, wherein the member has a tube shape and has such a shape as to be fitted in a cavum conchae.

4. The ear canal fitting unit according to claim 3, wherein the ear canal fitting unit is provided at a leading end of a hook-shape member capable of being hooked on a root of an auricle, and the hook-shape member is provided with an amplifier that amplifies potential difference between the electrode and a reference electrode provided at a tail end of the hook-shape member attachably to an earlobe.

5. An ear canal fitting unit comprising:

a tube configured to be capable of being inserted into an ear canal;

an electrode configured to have flexibility and be so disposed along an outer circumferential surface of the tube that a predetermined gap is formed between the electrode and an inner surface of the ear canal;

pressing means for deforming the electrode in such a direction as to get away from the outer circumferential surface of the tube and pressing the electrode against the inner surface of the ear canal; and suppressing means for suppressing push-back of the electrode pressed against the inner surface of the ear canal, wherein the suppressing means switches a degree of suppression of push-back in a stepwise manner, the tube is so formed by using a sponge material as to have an inner diameter larger than an inner diameter of the ear canal, the electrode is composed of plate-shape electrodes bonded to the outer circumferential surface of the tube at a predetermined interval, and the pressing means and the suppressing means are force of reversion of the tube that is compressed to an original state.

6. A biological signal measuring device comprising:

an ear hook component configured to have a flexible hook-shape part capable of being hooked on a root of an auricle;

an ear canal fitting unit configured to be provided at a leading end part of the hook-shape part and be fitted in an ear canal; and an earlobe attachment configured to be provided at a tail end part of the hook-shape part and be mounted on an earlobe, wherein the ear canal fitting unit has a tube capable of being inserted into the ear canal, an electrode that has flexibility and is so disposed along an outer circumferential surface of the tube that a predetermined gap is formed between the electrode and an inner surface of the ear canal, pressing means that deforms the electrode in such a direction as to get away from the outer circumferential surface of the tube and presses the electrode against the inner surface of the ear canal, and suppressing means that suppresses push-back of the electrode pressed against the inner surface of the ear canal, and the earlobe attachment has a reference electrode capable of being attached to the earlobe, and the ear hook component has an amplifier that amplifies potential difference between the electrode and the reference electrode as a biological signal.

7. The biological signal measuring device according to claim 6, wherein the ear canal fitting unit further has a speaker, and the ear hook component further has notifying means that notifies a message via the speaker if an average level of a biological signal in a predetermined period, of the biological signal amplified by the amplifier, is lower than a level under which the electrode should be regarded as being not in contact with the inner surface of the ear canal.

8. The biological signal measuring device according to claim 7, wherein the ear hook component further has a memory in which a biological signal having the average level equal to or higher than the level is stored.

\* \* \* \* \*